(12) United States Patent
Huang et al.

(10) Patent No.: US 8,076,142 B2
(45) Date of Patent: Dec. 13, 2011

(54) ROOTED PLANT ASSAY SYSTEM

(75) Inventors: Xiang Huang, Apex, NC (US); Ming Cheng, Cary, NC (US); Haiping Hong, Morrisville, NC (US); Yan Liu, Chapel Hill, NC (US); Kangfeng Mei, Apex, NC (US)

(73) Assignee: BASF Plant Sciences GmbH (DE)

( * ) Notice: Subject to any disclaimer, the term of this patent is extended or adjusted under 35 U.S.C. 154(b) by 345 days.

(21) Appl. No.: 12/001,234

(22) Filed: Dec. 11, 2007

(65) Prior Publication Data

US 2008/0153102 A1  Jun. 26, 2008

Related U.S. Application Data

(60) Provisional application No. 60/871,258, filed on Dec. 21, 2006.

(51) Int. Cl.
*C12N 15/82* (2006.01)
*C12N 5/04* (2006.01)
*A01H 5/00* (2006.01)

(52) U.S. Cl. ..... 435/469; 435/419; 800/294; 800/317.2; 800/312; 800/317.4

(58) Field of Classification Search .................. 435/220, 435/469, 419; 800/294, 317.2, 312, 317.4, 800/301, 279
See application file for complete search history.

(56) References Cited

FOREIGN PATENT DOCUMENTS

| EP | 0334383 | 3/1989 |
|---|---|---|
| WO | WO 00/12735 | 9/2000 |
| WO | WO 2006/024509 | 3/2006 |

OTHER PUBLICATIONS

Olhoft et al. L-Cysteine increases *Agrobacterium*-mediated T-DNA delivery into soybean cotyledonary-node cells. Plant Cell Rep (2001) 20:706-711.*
El-Shemy et al. Reproducible transformation in two grain legumes—soybean and akuzi bean using different system. Cellular & Molecular biology letters vol. 7, (2002) pp. 709-719.*
Peres,L.E. et al., Shoot regeneration capacity from roots and transgenic hairy roots of tomato cultivars and wild related species, Plant Cell Tissue 2001 65, 37-44.
Collier,R.et al., Ex vitro composite plants: an inexpensive, rapid method for root biology, The Plant Journal 2005 43, 449-457.
Simpson,R.et al., A disarmed binary vector from *Agrobacterium tumefaciens* functions in *Agrobacterium rhizogenes*, Plant Molecular Biology 1986 6, 403-415.

* cited by examiner

*Primary Examiner* — Annette Para
(74) *Attorney, Agent, or Firm* — Patricia A. McDaniels

(57) ABSTRACT

Disclosed herein are rooted plant assay systems, methods of making rooted plant assay systems, and methods of using rooted plant assay systems for high throughput screening of test polynucleotides for their ability to effect phenotypic traits having agricultural value.

4 Claims, No Drawings

ROOTED PLANT ASSAY SYSTEM

CROSS REFERENCE TO RELATED APPLICATIONS

This application claims the priority benefit of U.S. Provisional Application Ser. No. 60/871,258 filed Dec. 21, 2006.

FIELD OF THE INVENTION

The present invention relates to the field of agricultural biotechnology. Disclosed herein are rooted plant assay systems, methods of producing such rooted plant assay systems, and methods of using rooted plant assay systems for high throughput screening of genetically-induced phenotypic traits.

BACKGROUND OF THE INVENTION

Agricultural biotechnology has progressed significantly since the 1980s, allowing development of a number of improved genetically modified crop plants which demonstrate resistance to pests and improved tolerance to commercial herbicides. However, currently available model plant systems for screening transgenes are inefficient, requiring extensive time for generating transformants. In vitro model systems, such as hairy roots, may also exhibit variability which renders results difficult to interpret. In addition, a phenotype observed in a model plant or plant tissue transformed with a transgene may not be observed in a crop plant transformed with the same transgene. The drawbacks of existing model systems may be attributable in part to existing transformation methodology and in part to the nature of the plant or plant tissue being transformed.

WO 00/12735 discloses an assay for screening transgenes for functional activity that employs a stable chimeric plant having wild-type shoots, stems, and leaves, but having transgenic "hairy roots" (neoplastic outgrowths of fine roots caused by the soil bacterium *Agrobacterium rhizogenes*). In the assay of WO 00/12735, an explant of the plant species to be assayed is wounded, and the wounded portion is infected with *A. rhizogenes* that is "armed", i.e., capable of causing disease. The *A. rhizogenes* contains a transgene that may be incorporated into 40-90% of the hairy roots that form below the wounding site. Tissues above the wounding site are not infected by the *A. rhizogenes* and thus do not contain the transgene.

Commonly assigned WO 2006/024509 discloses "disarmed" strain variants of *A. rhizogenes* strain K599 useful for transforming plants to generate whole transgenic plants with normal (non-hairy) root phenotype. In the transformation methods of WO 2006/024509, after co-cultivation with *A. rhizogenes* strain K599, plant shoots are induced prior to root induction, and the ultimate transformed plant which is obtained is transgenic in all tissues.

Agricultural pests and climate change have negatively influenced humanity's ability to grow enough food to feed itself. In addition, the need to replace fossil fuels with more sustainable energy sources has made development of biofuels an important goal of the 21$^{st}$ century. A large number of transgenes must therefore be screened for functionality in crop plants in order to solve existing agricultural challenges. A need exists for improved methods to facilitate the ease, speed and efficiency of high throughput transformation systems for evaluating expression of transgenes that mediate a variety of root-specific phenotypic traits, including disease resistance, insect resistance, herbicide tolerance, abiotic stress tolerance, and the like.

SUMMARY OF THE INVENTION

The present inventors have found that it is possible to produce rooted plant assay systems which are wild type in all tissues other than root tissue, which is transgenic. The transgenic roots of the rooted plant assay systems of the invention are not hairy roots and thus are more closely representative of normal plant roots. The rooted plant assay systems of the invention are produced using disarmed *Agrobacterium* strains in combination with transformation techniques that omit a shoot induction step, wherein root formation is induced immediately after co-cultivation with the disarmed *Agrobacterium* strains that carry a transgene of interest.

Thus in a first embodiment, the invention provides a rooted plant assay system which is non-transgenic in all tissues other than roots, wherein said roots are transgenic non-hairy roots.

In another embodiment, the invention provides a method of making a rooted plant assay system comprising the steps of: obtaining a plant tissue explant; infecting said explant with disarmed *Agrobacterium rhizogenes* comprising transgenic T-DNA, wherein said T-DNA comprises a selectable marker gene and a test polynucleotide; growing the infected explant on a medium comprising: an effective amount of at least one root-inducing auxin compound and an effective amount of a selection agent; and, in a final step, selecting rooted plantlets that grow on said medium.

In another embodiment, the invention provides a method of making a rooted plant assay system comprising the steps of: obtaining a monocot embryonic tissue explant; infecting said explant with disarmed *Agrobacterium tumefaciens* comprising transgenic T-DNA, wherein said T-DNA comprises a selectable marker gene and a test polynucleotide; growing said infected explant on a medium comprising: an effective amount of a root-inducing auxin compound and an effective amount of a selection agent; and in a final step, selecting rooted plantlets that grow on said medium.

In yet another embodiment, the invention provides a method of making a rooted plant assay system comprising the steps of: obtaining a wounded dicot tissue explant; adding the explant to a disarmed *Agrobacterium tumefaciens* comprising a transgenic T-DNA, wherein said T-DNA comprises a selectable marker gene and a test polynucleotide, in a co-cultivation medium comprising a cytokinin to obtain an infected explant; growing said infected explant on a selection medium comprising: an effective amount of a root-inducing auxin compound and an effective amount of a selection agent; and, in a final step, selecting rooted plantlets that grow on said selection medium.

In another embodiment, the invention provides a method of screening for functionality of a test polynucleotide comprising the steps of: generating a rooted plant assay system having roots comprising the test polynucleotide; exposing the roots of the rooted plant assay system to a plant pathogen, an abiotic stress condition, a chemical, or a decreased nutrient condition; and assaying the rooted plant assay system for a response to said plant pathogen, said abiotic stress condition, said chemical, or said decreased nutrient condition.

DETAILED DESCRIPTION OF THE INVENTION

Unless otherwise noted, the terms used herein are to be understood according to conventional usage by those of ordinary skill in the relevant art. Definition of common terms in molecular biology may be found in many reference sources known to those of skill in the art, including but not limited to, Rieger et al., 1991 Glossary of genetics: classical and molecular, 5$^{th}$ Ed., Berlin: Springer-Verlag; and in Current Protocols in Molecular Biology, F. M. Ausubel et al., Eds., Current Protocols, a joint venture between Greene Publishing Associates, Inc., and John Wiley & Sons, Inc., (1998 Supplement).

It must be noted that as used herein and in the appended claims, the singular form "a", "an", or "the" includes plural reference unless the context clearly dictates otherwise. As used herein, the word "or" means any one member of a particular list and also includes any combination of members of that list.

As used herein, the word "nucleic acid", "nucleotide", or "polynucleotide" is intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, antisense sequences, and non-coding regulatory sequences that do not encode mRNAs or protein products. A "test polynucleotide" as defined herein is a polynucleotide that encodes or is believed to encode an agronomically valuable or a phenotypic trait. A test polynucleotide may comprise a gene, a fragment of a gene encoding a functional domain, an RNAi construct, an antisense construct, or any other polynucleotide whose activity is desired to be determined.

The term "gene" is used broadly to refer to any segment of nucleic acid associated with a biological function. Thus, genes may include introns and exons as in genomic sequence, or may comprise only a coding sequence as in cDNAs, and/or may include cDNAs in combination regulatory sequences.

The terms "polypeptide" and "protein" are used interchangeably herein to refer to a polymer of consecutive amino acid residues.

The term "cell" or "plant cell" as used herein refers to single cell, and also includes a population of cells. The population may be a pure population comprising one cell type. Likewise, the population may comprise more than one cell type. A plant cell within the meaning of the invention may be isolated (e.g., in suspension culture) or comprised in a plant tissue, plant organ or plant at any developmental stage.

The term "explant" as used herein refers to plant tissues, or plant organs that are separated from the whole plant or seed. For example, an explant may be the cotyledons alone containing the proximal end to the seedling that may contain cells capable of generating roots upon transformation with disarmed Agrobacterium; or an explant may be the portion or a whole plant or seedling above and including, the hypocotyl that may contain cells capable of generating roots upon transformation with disarmed Agrobacterium. The term "meristem" or "meristematic cells" or "meristematic tissue" can be used interchangeably and is intended to mean undifferentiated plant tissue, which continually divides, forming new cells, as that found at the tip of a stem or root.

The term "node" is intended to mean the point on a stem where a leaf is attached or has been attached. The term "internode" is intended to mean the section or part between two nodes on a stem.

The term "axillary bud" is intended to mean a small protuberance along a stem or branch, sometimes enclosed in protective scales and containing an undeveloped shoot, leaf, or flower; also called a lateral bud.

The term "petiole" is intended to mean the stalk by which a leaf is attached to a stem, also called a leaf-stalk. The term "leaf" as used herein refers to the vegetative organ attached to a stem via a petiole. A leaf, in the context of the present invention, may comprise a whole leaf with petiole attached, a leaf section, or a leaf section with petiole attached.

The term "hypocotyl" is intended to mean the part of the stem between the seed leaves (the cotyledons) and the root. The term "leaf axil" is intended to mean the angle between a leaf and the stem on which it is borne. The axillary bud occurs at the leaf axil.

The term "cotyledon" is intended to mean a leaf of the embryo of a seed plant, which upon germination either remains in the seed or emerges, enlarges, and becomes green, also called a seed leaf. The soybean seed consists of two seed/halves, which are cotyledons or seed leaves. The embryo axis is located between the cotyledons and is attached to them near the end closest to the micropyle.

The term "epicotyl" used herein refers to the part above the cotyledon of a plant seedling.

The term "transformation" as used herein refers to the introduction of genetic material (e.g., a transgene) into a cell, tissue or organ. Transformation of a cell, tissue or organ may be stable or transient. The term "transient transformation" refers to the introduction of one or more transgenes into a cell, tissue or organ in the absence of integration of the transgene into the host's genome. In contrast, the term "stable transformation" refers to the introduction and integration of one or more transgenes into the genome of a cell, tissue or organ, preferably resulting in chromosomal integration and stable heritability through meiosis.

Various explant tissues and transformation protocols suitable for use in the methods of the invention include, but are not limited to, callus (U.S. Pat. No. 5,591,616; EP-A1 604 662), immature embryos (EP-A1 672 752), pollen (U.S. Pat. No. 54,929,300), shoot apex (U.S. Pat. No. 5,164,310), or in planta transformation (U.S. Pat. No. 5,994,624). The methods of the present invention may be practiced using any *Agrobacterium* mediated transformation method known in the art. Preferred explant/transformation protocol combinations are set forth in Table 1.

TABLE 1

| Variety | Material/Citation |
| --- | --- |
| Monocotyledonous plants: | Immature embryos (EP-A1 672 752) |
| | Callus (EP-A1 604 662) |
| | Embryogenic callus (U.S. Pat. No. 6,074,877) |
| | Inflorescence (U.S. Pat. No. 6,037,522) |
| | Flower (in planta) (WO 01/12828) |
| Banana | U.S. Pat. No. 5,792,935; EP-A1 731 632; |
| | U.S. Pat. No. 6,133,035 |
| Barley | WO 99/04618 |
| Maize | U.S. Pat. No. 5,177,010; U.S. Pat. No. 5,987,840 |
| Pineapple | U.S. Pat. No. 5,952,543; WO 01/33943 |
| Rice | EP-A1 897 013; U.S. Pat. No. 6,215,051; |
| | WO 01/12828 |
| Wheat | AU-B 738 153; EP-A1 856 060 |
| Beans | U.S. Pat. No. 5,169,770; EP-A1 397 687 |
| *Brassica* | U.S. Pat. No. 5,188,958; EP-A1 270 615; |
| | EP-A1 1,009,845 |
| Cacao | U.S. Pat. No. 6,150,587 |
| Citrus | U.S. Pat. No. 6,103,955 |
| Coffee | AU 729 635 |
| Cotton | U.S. Pat. No. 5,004,863; EP-A1 270 355; |
| | U.S. Pat. No. 5,846,797; EP-A1 1,183,377; |
| | EP-A1 1,050,334; EP-A1 1,197,579; EP-A1 1,159,436 |
| | Pollen transformation (U.S. Pat. No. 5,929,300) |
| | In planta transformation (U.S. Pat. No. 5,994,624) |
| Pea | U.S. Pat. No. 5,286,635 |
| Pepper | U.S. Pat. No. 5,262,316 |
| Poplar | U.S. Pat. No. 4,795,855 |
| Soybean | cotyledonary node of germinated soybean seedlings |

TABLE 1-continued

| Variety | Material/Citation |
|---|---|
| | shoot apex (U.S. Pat. No. 5,164,310) |
| | axillary meristematic tissue of primary, or higher leaf node of about 7 days germinated soybean seedlings |
| | organogenic callus cultures |
| | dehydrated embryo axes |
| | U.S. Pat. No. 5,376,543; EP-A1 397 687; |
| | U.S. Pat. No. 5,416,011; U.S. Pat. No. 5,968,830; |
| | U.S. Pat. No. 5,563,055; U.S. Pat. No. 5,959,179; |
| | EP-A1 652 965; EP-A1 1,141,346 |
| Sugarbeet | EP-A1 517 833; WO 01/42480 |
| Tomato | U.S. Pat. No. 5,565,347 |

The term "transformation efficiency" as used herein can be measured by the number of transformed cells (or transformed organisms grown from individually transformed cells) that are recovered under standard experimental conditions.

The terms "infecting" and "infection" with a bacterium refer to co-incubation of a target biological sample (e.g., cell, tissue, organ) with the bacterium under conditions such that polynucleotides contained within the bacterium are introduced into one or more cells of the target biological sample.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. A vector can be a binary vector or a T-DNA that comprises the left border and the right border and may include a gene of interest or test polynucleotide between the left and right borders.

The term "promoter" as used herein refers to a DNA sequence which when ligated to a test polynucleotide is capable of controlling the transcription of the test polynucleotide.

The term "tissue" with respect to a plant (or "plant tissue") means multiple plant cells, including differentiated and/or undifferentiated tissues of plants. Plant tissues may constitute part of a plant organ (e.g., the epidermis of a plant leaf) but may also constitute tumor tissues (e.g., callus tissue) and various types of cells in culture (e.g., single cells, protoplasts, embryos, calli, protocorm-like bodies, etc.). Plant tissues include, but are not limited to, stems, roots, shoots, fruits, ovules, stamens, leaves, embryos, meristematic regions, callus tissue, gametophytes, sporophytes, pollen, microspores, hypocotyls, cotyledons, anthers, sepals, petals, pollen, seeds and the like. Plant tissues may be in planta, in organ culture, tissue culture, or cell culture.

The term "organ" with respect to a plant (or "plant organ") means parts of a plant and may include, but not limited to, for example roots, fruits, shoots, stems, leaves, hypocotyls, cotyledons, anthers, sepals, petals, pollen, seeds, etc., that contain cells capable of generating roots upon transformation with disarmed *Agrobacterium*.

The term "plant" as used herein can, depending on context, be understood to refer to whole plants, plant cells, plant organs, plant seeds, and progeny of same. The word "plant" also refers to any plant, particularly, to seed plant, and may include, but not limited to, crop plants. The class of plants is generally as broad as the class of higher and lower plants amenable to transformation techniques, including angiosperms (monocotyledonous and dicotyledonous plants), gymnosperms, ferns, horsetails, psilophytes, bryophytes, and multicellular algae. A plant as defined herein may be from any genus, including but not limited to *Medicago, Lycopersicon, Brassica, Cucumis, Solanum, Juglans, Gossypium, Malus, Vitis, Antirrhinum, Populus, Fragaria, Arabidopsis, Picea, Capsicum, Chenopodium, Dendranthema, Pharbitis, Pinus, Pisum, Oryza, Zea, Triticum, Triticale, Secale, Lolium, Hordeum, Glycine, Pseudotsuga, Kalanchoe, Beta, Helianthus, Nicotiana, Cucurbita, Rosa, Fragaria, Lotus, Medicago, Onobrychis, trifolium, Trigonella, Vigna, Citrus, Linum, Geranium, Manihot, Daucus, Raphanus, Sinapis, Atropa, Datura, Hyoscyamus, Nicotiana, Petunia, Digitalis, Majorana, Ciahorium, Lactuca, Bromus, Asparagus, Antirrhinum, Heterocallis, Nemesis, Pelargonium, Panieum, Pennisetum, Ranunculus, Senecio, Salpiglossis, Browaalia, Phaseolus, Avena,* and *Allium.*

The term "wild type" as used herein refers to a plant cell, an explant, seed, plant component, plant tissue, plant organ, or whole plant that has not been genetically modified or treated in an experimental sense.

The term "control" as used herein refers to a plant cell, an explant, seed, plant component, plant tissue, plant organ, or whole plant used to compare against transgenic or genetically modified plant for the purpose of identifying an enhanced phenotype or a desirable trait in the transgenic or genetically modified plant. A "control plant" may in some cases be a transgenic plant line that comprises an empty vector or marker gene, but does not contain the test polynucleotide that is present in the transgenic or genetically modified plant being evaluated. A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

The term "trait" as used herein refers to a physiological, morphological, biochemical, or physical characteristic of a plant or particular plant material or cell. In some instances, this characteristic is visible to human eyes, such as seed or plant size, or can be measured by biochemical techniques, such as detecting the protein, starch, or oil content of seed or leaves, or by observation of a metabolic or physiological process, for example, by measuring tolerance to water deprivation or particular salt or sugar concentrations, or by the observation of the expression level of a gene or genes, e.g., by employing Northern analysis, RT-PCT, microarray gene expression assays, or by agricultural observations such as osmotic stress tolerance or yield. Any technique can be used to measure the amount of, comparative level of, or difference in any selected chemical compound or macromolecule in the transgenic plants. A phenotypic trait includes, but is not limited to, increased yield, increased tolerance to stress conditions including drought, cold and salinity conditions, increased resistance or tolerance to insecticide, increased resistance or tolerance to herbicide, increased resistance or tolerance to nematodes, and increased nitrogen use efficiency.

The term "transgene" as used herein refers to any polynucleotide that is introduced into the genome of a cell by experimental manipulations. A transgene may be an "endogenous DNA", or a "heterologous DNA". "Endogenous DNA" refers to a polynucleotide that is naturally found in the cell into which it is introduced so long as it does not contain some modification relative to the naturally occurring polynucleotide. "Heterologous DNA" refers to a polynucleotide that is ligated to a polynucleotide to which it is not ligated in nature, or to which it is ligated at a different location in nature. Heterologous DNA is not endogenous to the cell into which it is introduced, but has been obtained from another cell. Heterologous DNA can include an endogenous DNA that contains one or more modifications.

The term "transgenic" as used herein is intended to refer to cells, tissues, and/or plants that contain a transgene, or whose genome has been altered by the introduction of a transgene, or that have incorporated exogenous genes or polynucleotides. Transgenic cells, tissues, organs and plants may be produced by several methods including the introduction of a transgene or test polynucleotide into a target cell or integration of the transgene or test polynucleotide into a chromosome of a target cell by way of human intervention, such as by the methods described herein.

As used herein, "RNAi" or "RNA interference" refers to the process of sequence-specific post-transcriptional gene silencing, mediated by double-stranded RNA (dsRNA). As used herein, "dsRNA" refers to RNA that is partially or completely double stranded. Double stranded RNA is also referred to as small or short interfering RNA (siRNA), short interfering nucleic acid (siNA), short interfering RNA, micro-RNA (miRNA), and the like. In the RNAi process, dsRNA comprising a first strand that is substantially identical to a portion of a target gene and a second strand that is complementary to the first strand is introduced into a host cell. After the introduction, the target gene-specific dsRNA is processed into relatively small fragments (siRNAs) by RNAi processing enzymes present in the host cell and can subsequently become distributed throughout the host cell, leading to a loss-of-function mutation having a phenotype that, over the period of a generation, may come to closely resemble the phenotype arising from a complete or partial deletion of the target gene.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. As used herein, the term "substantially complementary" means that two nucleic acid sequences are complementary at least at 80% of their nucleotides. Preferably, the two nucleic acid sequences are complementary at least at 85%, 90%, 95%, 96%, 97%, 98%, 99% or more of their nucleotides. Alternatively, "substantially complementary" means that two nucleic acid sequences can hybridize under high stringency conditions. As used herein, the term "substantially identical" or "corresponding to" means that two nucleic acid sequences have at least 80% sequence identity. Preferably, the two nucleic acid sequences have at least 85%, 90%, 95%, 96%, 97%, 98%, 99% or 100% sequence identity.

An "antisense" nucleic acid comprises a nucleotide sequence that is complementary to a "sense" nucleic acid encoding a protein, e.g., complementary to an mRNA sequence. Accordingly, an antisense nucleic acid can hydrogen bond to a sense nucleic acid. The antisense nucleic acid can be complementary to an entire target gene, or to a portion thereof. The antisense nucleic acid molecules are typically administered to a cell or generated in situ such that they hybridize with or bind to cellular mRNA and/or genomic DNA. Hybridization may be performed under stringent conditions, e.g., 400 mM NaCl, 40 mM PIPES pH 6.4, 1 mM EDTA, 60° C. hybridization for 12-16 hours; followed by washing at 65° C. with 0.1% SDS and 0.1% SSC for about 30-60 minutes.

Standard techniques for cloning, DNA and RNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook and Russell, 2001 Molecular Cloning, Third Edition, Cold Spring Harbor Laboratory, Plainview, N.Y.; Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Harnes and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

In a first embodiment, the invention provides a "rooted plant assay system" that is, a chimeric plant assay system in which all tissues except the roots are non-transgenic. The roots of the rooted plant assay system as defined herein are transgenic and have normal, non-hairy root physiology. Any transgene or test polynucleotide may be transformed into the roots of the rooted plant assay system of the invention, using the methods taught herein. The rooted plant assay system of the invention is suitable for high-throughput screening of transgenes or test polynucleotides having particular or specific functionality in roots.

In accordance with the invention, the rooted plant assay system may be derived from any plant. For example, the plant may be selected from the group consisting of monocotyledonous plants, dicotyledonous plants, and gymnosperm plants. Non-limiting examples of plants from which the rooted plant assay system may be derived include maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula*, prerennial grass, ryegrass, *Arabidopsis thaliana*, and the like.

The invention is also embodied in a method for producing the rooted plant assay system of the invention, which employs transformation using disarmed *A. rhizogenes* such as a non-pathogenic strain variant of *Agrobacterium* strain K599 (WO2006/024509) or a derivative of that strain which is capable of infecting plant tissues but is lacking hairy root phenotype inducing properties. This method is suitable for making rooted plant assay systems that are derived from dicotyledenous plants or from monocotyledonous plants.

In the first step of this embodiment, a plant tissue explant is obtained. When the rooted plant assay system is derived from a dicotyledenous plant, the explant is a wounded explant such as a hypocotyl, cotyledon, leaf section, or petiole with leaf blade. When the rooted plant assay system is derived from a monocot, the explant is preferably an immature embryo.

In the second step of this embodiment, the explant is infected with disarmed *A. rhizogenes* comprising transgenic T-DNA, wherein the T-DNA comprises a selectable marker gene and a test polynucleotide. Any selectable marker gene may be used in the T-DNA: for example, the selectable marker gene may be a mutant acetohydroxyacid synthase (AHAS; EC 4.1.3.18, also known as acetolactate synthase or ALS) gene that confers resistance to imidazolinones, or a mutant BAR gene that confers resistance to glufosinate, or a mutant ESPS gene that confers resistance to glyphosate, or an nptII gene that confers resistance to kanamycin, and the like.

In the third step of this embodiment, the infected explant is grown on a medium comprising an effective amount of at least one root-inducing auxin compound in combination with an effective amount of a selection agent. As used herein, an "effective amount of at least one root-inducing auxin compound" means that amount of root-inducing auxin compound, whether a single auxin or more than one auxin, which is sufficient to induce root formation. An "effective amount of a selection agent" means the amount of selection agent necessary to kill cells that have not incorporated the transgene while allowing cells that have incorporated the transgene to survive. Root-inducing auxins suitable for use in the medium include indole-3-acetic acid (IAA), indole-3-butyric acid (IBA), 2-phenyl acetic acid (PAA), napthalene acetic acid (NAA), 4-chorophenoxy acetic acid (4-CPA), 2,4-dichlorophenoxy acetic acid (2,4-D), 2,4,5-trichlorophenoxy acetic acid (2,4,5,-T), 3,6-dichloro-2-methoxybenzoic acid (dicamba), and 4-amino-3,5,6-trichloro-2-pyridinecarboxylic acid (picloram). Any selection agent may be used in accordance with the invention, so long as the selection agent corresponds to the selectable marker gene as indicated above.

In the final step of this embodiment, rooted plantlets that grow on the auxin/selection medium are distinguished from plantlets that do not contain roots, and selected for further use.

In another embodiment, the invention provides a method of making a rooted plant assay system which employs a disarmed *A. tumefaciens* such as strains AGL1 or EHA101 or their derivatives. This embodiment of the method of the invention is suitable for making rooted plant assay systems derived from monocots. In the first step of this embodiment, a monocot embryonic tissue explant is obtained. In the second step, the monocot embryonic tissue explant is infected with disarmed *A. tumefaciens* comprising transgenic T-DNA, wherein said T-DNA comprises a selectable marker gene and a test polynucleotide. In the third step, the infected explant is grown on a medium comprising an effective amount of a root-inducing auxin compound and an effective amount of a selection agent. In the final step, rooted plantlets that grow on the auxin/selection medium are distinguished from plantlets that do not contain roots, and selected for further use.

In yet another embodiment, the invention provides a method of making a rooted plant assay system employing disarmed *A. tumefaciens* and a cytokinin. This method is suitable for making rooted plant assay systems derived from dicots. In the first step, a wounded dicot tissue explant is obtained. In the second step of this embodiment, the wounded explant is added to a disarmed *A. tumefaciens* comprising a transgenic T-DNA comprising a selectable marker gene and a test polynucleotide, in a co-cultivation medium comprising a cytokinin. Cytokinins are well known in the art of plant transformation, and they include, without limitation (BAP) and kinetin. In the third step of this embodiment, the infected explant is grown on a selection medium comprising an effective amount of a root-inducing auxin compound and an effective amount of a selection agent. In the final step, rooted plantlets that grow on the auxin/selection medium are distinguished from plantlets that do not contain roots, and selected for further use.

In another embodiment, the invention provides a method of screening for functionality of a test polynucleotide. In accordance with the invention, any test polynucleotide may be assayed using the rooted plant assay system of the invention. In the first step of this embodiment, a rooted plant assay system having roots comprising the test polynucleotide is generated. In the second step of this embodiment, the roots of the rooted plant assay system are exposed to a plant pathogen, an abiotic stress condition, a chemical, or a decreased nutrient condition. In the third step of this embodiment, the rooted plant assay system is assayed for a response to the plant pathogen, abiotic stress condition, chemical, or decreased nutrient condition. The rooted plant assay systems or portions thereof that resist the plant pathogen or survive the abiotic stress condition, chemical, or decreased nutrient condition are distinguished from rooted plant assay systems or portions thereof that do not resist the plant pathogen or survive the abiotic stress condition, chemical, or decreased nutrient condition, and selected for further study.

One of the important uses of the present invention concerns screening for plant pathogen resistance-conferring polynucleotides. Potential plant pathogen resistance polynucleotides include RNAi constructs and genes that confer resistance to nematodes. Nematodes are microscopic wormlike animals that feed on roots, leaves, and stems of more than 2,000 vegetables, fruits, and ornamental plants. One common type of nematode is the root-knot nematode, whose feeding causes the characteristic galls on roots. Other root-feeding nematodes are the cyst- and lesion-type, which are more host specific. Signs of nematode damage include stunting and yellowing of leaves, and wilting of the plants during hot periods. However, nematodes, including soybean cyst nematode (SCN), can cause significant yield loss without obvious above-ground symptoms. In addition, roots infected with SCN are dwarfed or stunted. SCN can decrease the number of nitrogen-fixing nodules on the roots, and may make the roots more susceptible to attacks by other soil-borne plant pathogens.

A difficulty in finding agents that are active against SCN has been establishing an efficient, reproducible, and convenient bioassay method. While SCN can be propagated on normal soybean plant roots, this technique requires the continual establishment of root explants because these organs have a determinant period of growth in culture. An alternative system, soybean hairy roots generated by infecting soybean cotyledons with wild type *A. rhizogenes*, exhibits indeterminate growth in tissue culture providing an alternative to normal whole plant roots for study of SCN. However, hairy roots can interfere with the screening assay for nematode resistant phenotypes, and more particularly with the determination of root morphology and normal root resistance conferred by the test polynucleotide. The rooted plant assay systems produced by the present invention provide normal roots for more reliable screening of test polynucleotides that have the potential to confer resistance to nematodes.

Another important use for the rooted plant assay system of the invention is to screen for genes related to nitrogen use efficiency and nitrogen fixation. In many natural environments, availability of nitrogen is the primary factor limiting plant growth and productivity. Metabolism, growth and development of plants are profoundly affected by their nitrogen supply. Restricted nitrogen supply alters shoot to root ratio, root development, activity of enzymes of primary metabolism and the rate of senescence of older leaves.

Increased nitrogen use efficiency by plants should enable crops to be cultivated with lower nitrogenous fertilizer input, or alternatively, on soils of poorer quality and would therefore have significant economic impact in both developed and developing agricultural systems. The present invention provides a high throughput system for screening nitrogen usage of a plant by producing rooted plant assay systems having a normal root phenotype.

Further, the present invention may be used to screen genes encoding proteins characterized as having potential herbicidal activity. For example, AHAS is the first enzyme that catalyzes the biochemical synthesis of the branched chain amino acids valine, leucine and isoleucine. AHAS is the site of action of four structurally diverse herbicide families including sulfonylureas, imidazolinones, triazolopyrimidines, and pyrimidyloxybenzoates. Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. The rooted plant assay system of the invention may be used to facilitate screening for new AHAS mutations and for new chemicals that interact with AHAS.

One of the most economically relevant traits is yield. A trait resulting in stress tolerance can also result in increased yield. Plant root systems are fundamental to the proper growth and development of all terrestrial plant species. In addition to the uptake of water and nutrients and providing physical support, roots mediate a complex but poorly understood exchange of communication between soil microbes and other plants. In agronomic systems, production is impacted by the availability of water and nutrients in the soil: root growth has a direct or indirect influence on growth and yield of aerial organs, particularly under conditions of nutrient limitation. Roots are also relevant for the production of secondary plant products, such as defense compounds and plant hormones. Establishment of proper root architecture is an important factor for the plant to effectively use the water and nutrients available in the environment and to maximize plant growth and production. In addition, under conditions of drought, roots can adapt to continued growth while at the same time producing and sending early warning signals to shoots which inhibit plant growth above ground. The present invention may also be used for screening test polynucleotides that function to improve a plant's ability to tolerate various environmental stresses such as, but not limited to, drought, excess moisture, limited nutrients, cold, chilling, freezing, high temperature, salt, and oxidative stress.

Root architecture is an area that has remained largely unexplored through classical breeding because of difficulties with assessing this trait in the field. Improved root growth of crop plants will also enhance competitiveness with weedy plants and will improve growth in arid areas, by increasing water accessibility and uptake. Improved root growth is also relevant for ecological purposes, such as bioremediation and prevention/arrest of soil erosion. Longer roots can alleviate not only the effects of water depletion from soil but also improve plant anchorage and standability, thus reducing lodging. Also, longer roots have the ability to cover a larger volume of soil and improve nutrient uptake. Therefore, altering root biomass, and in particular increasing root length, will improve plant growth as well as increase crop yield. The rooted plant assay system of the invention and methods of using the same in high throughput screening analysis will have significant impact on the ability to develop crop plants with improved root architecture through genetic manipulation.

The invention is further illustrated by the following examples, which are not to be construed in any way as imposing limitations upon the scope thereof.

EXAMPLES

Example 1

Rooted Plant Assay System Derived from Soybean Using Disarmed *A. rhizogenes*

Clean soybean seeds from soybean cultivar were sterilized in a chamber with chlorine gas produced by adding 3.5 ml 12N HCl drop wise into 100 ml bleach. All operations were conducted in a fume hood. After 24 hours in the chamber, seeds were removed and used immediately or stored at room temperature until use. Discolored seeds or cracked seeds were removed. To imbibe seeds, warm GM medium was poured around seeds until the seeds were entirely covered by the medium. Seedlings were grown in the light for 5-7 days until the epicotyl was extended beyond the cotyledons. Seedlings can be stored at 4° C. overnight before being used in transformation. The Germination Medium (GM) comprises: 1×B5 salts and vitamins, 1×MS iron stock, 2% sucrose, and 0.8% Noble agar at pH 5.8. As an alternative, soybean seeds can be germinated in 1% agar (50 ml) in Petri dishes for 7 days before *Agrobacterium* inoculation.

Three days before inoculation, a disarmed *Agrobacterium* culture, for example, the disarmed *A. rhizogenes* strain K599 liquid culture, was placed in 5 ml LB+Kan50 (containing 50 ug/ml Kanamycin) media in a 28° C. shaker (225 rpm) overnight. The next day, 1 ml of the culture was taken and spread onto an LB+Kan50 agar plate. The plates were incubated in a 28° C. incubator for two days. At the end of the two-day period the plates were covered with thick colonies. One plate was prepared for every 50 explants to be inoculated.

Alternatively, the disarmed *A. rhizogenes* strain K599 liquid culture was placed in LB+Kan50 (containing 50 ug/ml Kanamycin) media in a 28° C. shaker (225 rpm) overnight. Twenty-five milliliters of liquid culture was used for every 50 explants to be inoculated.

Soybean seedlings had elongated hypocotyls approximately 3 to 5 cm in length with visible epicotyls. The explants were then prepared by removing the epicotyls and part of the hypocotyls. The explant contained one or two cotyledons, an axillary meristem and the hypocotyl about 0.5 cm to about 3 cm in length. The seed coat was removed to facilitate cotyledon development. The cut end of the hypocotyl was the target for transformation/infection.

Alternatively, cotyledons containing the proximal end from its connection with the seedlings were used as another type of explant for transformation. The cut end was the target for *Agrobacterium* inoculation.

After the explants were cut off the seedlings, the cut end was immediately dipped onto the disarmed thick *A. rhizogenes* colonies prepared above so that the colonies were visible on the cut end. Alternatively, the explants can be immersed in the disarmed *A. rhizogenes* liquid culture for 30 minutes. The explants were then placed onto 1% agar in Petri dishes for co-cultivation. Approximately 10 explants were placed in one dish. The dishes were sealed with Saran wrap and co-cultured at 25-27° C. under light for 6-8 days.

After the transformation and co-cultivation step, soybean explants were transferred to rooting induction medium with a selection agent, for example, S-B5-605 or S-B5-607 for Bar gene selection (De Block et al., EMBO J. 6:2513-2518, 1987), or S-B5-708 for an AHAS mutant gene (Sathasivan et al., Plant Phys. 97:1044-50, 1991) selection, in Petri dishes. The cut end was inserted into the medium so that the callus developed from the cut end in the future was just below the medium surface. Six to nine explants were placed in each Petri dish. Cultures were maintained in the same condition as in the co-cultivation step.

The S-B5-605 medium comprises: 0.5×B5 salts, 3 mM MES, 2% sucrose, 1×B5 vitamins, 400 µg/ml Timentin, 0.8% Noble agar, 1 mg/l IBA and 3 µg/ml Glufosinate Ammonion (selection agent for Bar gene) at pH 5.8. The S-MS-607 medium comprises: 0.2×MS salts and B5 vitamins, 2% sucrose, 400 mg/l Timentin, and 3 mg/L Glufosinate Ammonium at pH5.8. The S-B5-708 medium comprises: 0.5×B5 salts, 3 mM MES, 2% sucrose, 1×B5 vitamins, 400 µg/ml Timentin, 0.8% Noble agar, and 1 µM Imazapyr (selection agent for AHAS gene) (BASF Corporation, Florham Park, N.J.) at pH5.8.

Two to three weeks after the selection and root induction, transformed roots were formed on the cut ends of the explants. For Bar gene selection, explants were transferred to root elongation medium (S-MS-607 medium supplemented with 3 mg/l Glufosinate Ammonion and 400 mg/l Timentin, without IBA) for further selection. Elongated roots located on the tissues above the callus were removed during the transfer. For AHAS mutant gene selection, explants were transferred to the same selection medium (S-B5-708 medium) for further selection. Transgenic roots proliferated well within one week in the medium and were ready to be subcultured.

Strong and white soybean roots were excised from the rooted explants and cultured in root growth medium supplemented with 200 mg/l Timentin (S-MS-606 medium) in either six-well plates or Petri plates. Cultures were maintained at room temperature under the dark condition. Subcultured roots in each well would vigorously grow lateral roots. The S-MS-606 medium comprises: 0.2×MS salts and B5 vitamins, 2% sucrose, and 200 mg/l Timentin at pH5.8.

Example 2

Auxin Effect on Transformation Efficiency in Soybean Explants

As shown in Example 1, soybean explants such as hypocotyls and cotyledons were selected in medium containing no auxin or a low concentration of auxin such as 1 mg/l IBA. The transformation efficiencies between those two treatments were similar. However, when high concentration of IBA such as 3 to 5 mg/l or a more potent auxin such as NAA (1 mg/l) was present in the medium, transformation efficiency was dramatically increased. For example, using cotyledons from William 82 as the explants, the transformation efficiency doubled in the treatments containing 3 mg/l IBA or 1 mg/l NAA compared to the control where no auxin was present in the medium. Furthermore, more transgenic roots were obtained from individual explants. For example, more than 20 transgenic roots (most of them were independent events) were obtained from hypocotyl explants when the infected explants were cultured and selected in the medium containing 1 mg/l NAA while 1-5 transgenic roots were obtained in the control where 0-1 mg/l IBA was present in the rooting induction and selection medium.

Example 3

Soybean Rooted Plant Assay System Produced Using Disarmed *A. tumefaciens*

Disarmed *A. tumefaciens* AGL1 (Lazo et al., Bio/Technology 9: 963-967 1991) harboring a plasmid vector containing a test polynucleotide (a gene encoding GUS) was used to transform soybean hypocotyl explants as described in Example 1. Explants were inoculated in liquid *Agrobacterium* suspension for 30 min, and then transferred to medium containing MS salts and B5 vitamins and 3 to 5 mg/l benzyl adenine (BA). The explants were co-cultured with *A. tumefaciens* for 4 days. After co-culture, primary roots formed on hypocotyl explants were removed. Explants were transformed to S-B5-605 lacking glufosinate for recovery for two days. Explants were finally transferred to rooting medium S-B5-605 for transgenic root selection. Transgenic roots were regenerated four weeks after selection. GUS activity was detected in the transgenic roots.

Example 4

Use of Soybean Plant Assay System to Detect Resistance to SCN Infection

One to five days after subculturing, roots of the soybean rooted plant assay system were inoculated with surface-decontaminated race 3 of SCN second stage juveniles (J2) at the level of 500 J2/well, in multi-well plates. The test polynucleotide was either an RNAi construct or a promoter-GUS construct. As a control, soybean cultivar Williams 82 control vector and Jack control vector roots were used. The plates were then sealed and incubated at 25-27° C. in the dark. Several independent root lines were generated from each binary vector transformation and the lines were used for bioassay. Four weeks after nematode inoculation, the cysts in each well were counted. A number of RNAi constructs were found to have activity in reducing cysts. A number of promoters were shown to have activity specifically in SCN feeding sites.

Example 5

Screening for Herbicide Resistance Using the Soybean Rooted Plant Assay System

The soybean rooted plant assay system containing transgenic roots were used as a quick screening method for different AHAS mutants conferring various degrees of herbicide resistance. AHAS genes containing single and double mutations were driven by a parsley ubiquitin promoter (WO03/102198). These constructs were transformed into soybean explants, for example, into hypocotyls as described above. Inoculated hypocotyls were selected on various concentrations of herbicide, e.g. 1 µM and 2 µM imazapyr, for AHAS gene selection. Three weeks following the induction in the root induction medium, the number of explants producing roots and the length of the roots were recorded.

An AHAS gene containing a double mutation driven by the parsley ubiquitin promoter was found to have the highest transformation efficiency, and the rooted explants generated thereof exhibited longer roots than the rooted explants transformed with other AHAS mutant genes under both herbicide pressures. The longer roots in vitro is a good indication of stronger resistance to the herbicide at whole plant level.

Example 6

Maize Rooted Plant Assay System

A. tumefaciens [LBA4404(pSB1)] harboring a binary vector containing the GUS or DSRed2 (Matz et al., Nature Biotechnol. 17:969-973, 1999; Lukyanov et al., J. Bio. Chem. 275 (34):25879) reporter gene and the maize ahas (U.S. Pat. No. 6,653,529) or dsdA (Erikson et al., Plant Mol. Biol. 57:425-433, 2005) selection gene were grown on solid B-YP-002 or B-LB-003 medium supplemented with appropriate antibiotics for 1-2 days. Two loops of Agrobacterium cells were collected and suspended in 2 ml M-LS-002 medium in a sterile 2 ml tube. The Agrobacterium suspension was kept on a shaker for 5 minutes to three hours at 1,000 rpm until use. The M-LS-002 medium comprises: 1×MS salts, 36 g/l glucose, 68.5 g/l sucrose, 1.5 mg/l 2.4 D, 0.5 mg/l nicotinic acid, 0.5 mg/L pyridoxine HCl, 1 mg/l thiamine HCl, 100 mg/l myo-inositol, 1 g/l casamino acid and 200 µM acetosyringone (pH 5.2). B-YP-002 medium comprises: 5 g/l yeast extract, 10 g/l Peptone, 5 g/l NaCl, 12 g/l agar, 50 mg/l spectinomycine and 10 mg/l tetracycline. The B-LB-003 medium comprises: 37 g/l LB agar and 50 ug/l Kanamycin.

Corn cobs, such as inbred genotype J553, were harvested at 8 to 11 days after pollination (when the immature embryos were between 0.6-2 mm in length). The cobs were sterilized in 20% Clorox solution for 5-10 min followed by spraying with 70% Ethanol, then thoroughly rinsed with sterile water. Immature embryos were dissected into the Agrobacterium suspension described above.

Agro-infection was carried out by inverting the tube several times. Approximately 1 ml of agro suspension was removed. The remaining mixture of Agrobacterium and explants was poured onto three layers of filter paper (Whatman #4) in a Petri dish. After the agro-solution was absorbed, the top layer of the filter paper with embryos was moved onto co-cultivation medium. The embryos were checked under microscope to assure that embryos were oriented with the scutellum side up. Co-culture was performed in the dark at 22° C. for 3 days. The Co-cultivation medium comprises: 1×MS salts, 10 g/l glucose, 20 g/l sucrose, 0.5 mg/l 2,4 D, 0.5 mg/l nicotinic acid, 0.5 mg/l pyridoxine HCl, 1 mg/l thiamine HCl, 100 mg/l myo-inositol, 700 mg/l L-proline, 500 mg/l MES, 200 µM acetosyringone, 15 M $AgNO_3$ and 1-1.2% agar (pH 5.8).

Embryos were transferred to recovery medium without selection (M-MS-101). Four to seven days later, they were transferred to rooting induction medium with a selection agent, such as d-Serine or Pursuit (M-MS-621 or M-MS-620), plus 0.0, 0.2, 0.5, or 1.0 mg/l NAA. The cultures were grown under dark conditions at 27° C. Transformed roots were generated from the explants within 2 to 4 weeks. Explants forming roots were transferred to fresh M-MS-621 or M-MS-620 medium or S-B5-102 with either 750 µM imazethapyr (BASF Corp, Florham Park, N.J.) or 10 mM d-serine as selection for root elongation. Roots were assessed to be transgenic using GUS or DsRed2 expression analysis or molecular analysis. Transformation efficiency ranged from 5 to 50% depending on the maize genotypes used.

The M-MS-101 medium comprises: 1×MS salt, 1×MS vitamins, 30 g/l sucrose, 100 mg/l Casein hydrolysate, 2.9 g/l proline, 1.5 mg/l 2,4-D, 15 µM $AgNO_3$, 150 mg/l timentin, and 0.2% Gelrite (PH 5.8). The M-MS-621 medium comprises: ¾×MS salts, 20 g/l sucrose, 0.5 mg/L nicotinic acid, 0.5 mg/l pyridoxine HCl, 1 mg/l thiamine HCl, 100 mg/l myo-inositol, 500 mg/l MES, 15 µM $AgNO_3$, 150 mg/l timentin, and 0.2% Gelrite (pH 5.8). The M-MS-620 medium is the same as M-MS-621 except that M-MS-620 contains 750 nM imazethapyr instead of 10 mM d-Serine. The S-B5-102 medium comprises: 1×B5 salts/iron/vitamins, 20 g/l sucrose, 8 g/l agar (PH5.8).

Example 7

Potato Rooted Plant Assay System

Leaf sections or petiole with leaf blade were cut from in vitro propagated potato plantlets, and pre-cultured in MS medium supplemented with 1 mg/l IBA or 0.1 to 0.5 mg/L NAA and BA, respectively. After 1-2 days, the explants were inoculated with disarmed A. rhizogenes harboring a binary vector containing a selectable gene such as Bar or AHAS. Explants were immersed in Agro suspension medium ($OD_{660}$=0.01-0.05) for 10 min, and then blotted dry using sterile filter paper. Infected explants were placed back to the pre-culture medium and co-cultured under light conditions as described in Example 1. After 2-3 days, explants were transferred to B5 medium with 200 mg/l Timetin and cultured for 3-4 days. After recovery, explants were selected in ½ B5 medium containing a selection agent such as 5-300 µM imazamox (BASF Corp, Florham Park, N.J.), transgenic roots were regenerated mostly from the med-vem region or the petioles of the explants. The average transformation efficiency was approximately 10%. Transgenic roots were used for promoter assay and nematode infection assay. GUS expression was detected in the roots. Root knots were formed after 5 days of infection with Meloidene incognita.

Example 8

Tomato Rooted Plant Assay System

Tomato seeds cv. Moneymaker and Roma VFN were sterilized in 70% ethanol for 30 seconds, and followed by soaking in 10% bleach for 5 minutes. Seeds were washed 3 times using sterile water. All operations were conducted in a fume hood. Seedlings were grown in the light for 7 days until the epicotyls were extended beyond the cotyledons. The germination medium comprises: 1×B5 salts and vitamins, 1× MS iron stock, 2% sucrose, and 0.8% Noble agar at pH 5.8.

Single colonies of disarmed A. rhizogenes culture harboring a plasmid containing the GUS gene and the AHAS selection gene, or a native A. rhizogenes strain harboring a plasmid containing the GUS gene and the Bar selection gene were inoculated into 3 ml of LB+Kan50 liquid medium. The cultures were grown in a 28° C. shaker at 225 rpm overnight. The next day, 0.5 ml of the cultures was taken and spread onto LB+Kan50 agar plates. The plates were incubated in 28° C. incubator for two days. At the end of the two-day period, the plates were covered with thick colonies.

Tomato seedlings prepared as above had elongated hypocotyls approximately 4 to 6 cm in length with visible epicotyls. The explants were then prepared by cutting the hypocotyls about 1 cm below cotyledons. The explants contained epicotyls, two cotyledons, and the hypocotyls about 1.5 cm in length. The cut end of the hypocotyls was the target for Agrobacterium transformation.

Alternatively, cotyledons containing the proximal end from its connection with the seedlings were used as another type of explants for transformation. The cut end was the target for Agrobacterium inoculation.

After the explants were cut off the seedlings, the cut end was immediately dipped onto the thick A. rhizogenes colonies prepared as described above so that the colonies were visible on the cut end. The explants were then placed onto 1% agar in Petri dishes for co-cultivation. The dishes were sealed with Saran wrap and co-cultured at 25-27° C. under light for 6 days.

After co-culture, explants were transferred to recovery media (S-B5-411) in Petri dishes. The cut end of the hypocotyls or cotyledons were inserted into the recovery media. Cultures were maintained at 27° C. under light at 30~50 μmol $m^{-2} S^{-1}$ for 3 days. The development of the callus at the end of cut was visible during this period. The S-B5-411 medium comprises: 0.5×B5 salts, 3 mM MES, 2% sucrose, 1×B5 vitamins, 400 μg/ml Timentin, 0.8% Noble agar at pH 5.8.

After the recovery step, tomato explants were transferred to root induction medium with a selection-agent, for example, S-B5-605 for Bar gene selection or S-B5-708 for an AHAS gene selection. The cut end with visible callus was inserted just below the surface of the media. Cultures were maintained in the same condition as in the recovery step. Transformed roots were generated in 2-3 weeks.

Strong and white roots were excised from the rooted explants and cultured in root growth media (S-MS-606) in either six-well plates or Petri plates. Cultures were maintained at 27° C. under the dark condition. The S-MS-606 medium comprises: 0.2×MS salts and B5 vitamins, 2% sucrose, and 200 mg/l Timentin at pH5.8.

One day after subculturing, the roots were inoculated with nematode RKN juveniles (J2) at the level of 500 J2/root. The plates were then sealed and put back into the incubator at 27° C. in dark. Nematode infection was monitored after 14 day incubation period. The rooted explants containing regenerated roots were analyzed using standard GUS staining protocol. The regenerated roots were immersed into the GUS solution, and left at 37° C. overnight. The stained roots were washed using 70% ethanol 3 times. Transgenic roots were confirmed by visual observation of root tissues with GUS positive blue color.

The invention claimed is:

1. A method of making a rooted plant assay system consisting of the steps of:
    a) obtaining a plant tissue explant;
    b) infecting said explant with disarmed *Agrobacterium rhizogenes* comprising transgenic T-DNA, wherein said T-DNA comprises a selectable marker gene and a test polynucleotide,
    c) growing the infected explant on a medium comprising:
        i) an effective amount of at least one root-inducing auxin compound, and
        ii) an effective amount of a selection agent; and
    d) selecting transgenic non-hairy roots that grow on said medium.

2. The method of claim 1, wherein the plant tissue explant is a wounded dicot tissue or a monocot embryonic tissue.

3. The method of claim 2, wherein the wounded dicot tissue is a soybean hypocotyl, a soybean cotyledon, a potato leaf section, a potato petiole, a tomato hypocotyl, or a tomato cotyledon.

4. A method of making a rooted plant assay system consisting of the steps of:
    e) obtaining a wounded dicot tissue explant;
    f) adding the explant to a disarmed *Agrobacterium tumnefaciens* comprising a transgenic T-DNA, wherein said T-DNA comprises a selectable marker gene and a test polynucleotide, in a co-cultivation medium comprising a cytokinin obtain an infected explant;
    g) growing said infected explant on a selection medium comprising:
        i) an effective amount of a root-inducing auxin compound, and
        ii) an effective amount of a selection agent; and
    h) selecting transgenic non-hairy roots that grow on said selection medium.

* * * * *